US008858437B2

(12) United States Patent
Pedrizzetti et al.

(10) Patent No.: US 8,858,437 B2
(45) Date of Patent: Oct. 14, 2014

(54) METHOD OF TRANSFORMING A DOPPLER VELOCITY DATASET INTO A VELOCITY VECTOR FIELD

(75) Inventors: Gianni Pedrizzetti, Prato (IT); Giovanni Tonti, Sulmona (IT)

(73) Assignees: Tomtec Imaging Systems GmbH (DE); Amid S.R.L. (IT)

( * ) Notice: Subject to any disclaimer, the term of this patent is extended or adjusted under 35 U.S.C. 154(b) by 124 days.

(21) Appl. No.: 13/449,634

(22) Filed: Apr. 18, 2012

(65) Prior Publication Data
US 2012/0265075 A1    Oct. 18, 2012

(30) Foreign Application Priority Data

Apr. 18, 2011 (EP) .................................... 11162845

(51) Int. Cl.
- *A61B 8/00* (2006.01)
- *G01S 15/89* (2006.01)
- *G06T 11/20* (2006.01)
- *A61B 8/06* (2006.01)

(52) U.S. Cl.
CPC ............... *A61B 8/06* (2013.01); *G01S 15/8984* (2013.01); *G06T 11/206* (2013.01); *G06T 2207/10132* (2013.01); *G06T 2207/30104* (2013.01)
USPC ............ 600/437; 600/407; 600/438; 600/441

(58) Field of Classification Search
USPC .................................. 600/407, 437, 441, 453
See application file for complete search history.

(56) References Cited

U.S. PATENT DOCUMENTS

| | | | |
|---|---|---|---|
| 5,357,964 A | 10/1994 | Spivey et al. | |
| 5,855,557 A * | 1/1999 | Lazenby | 600/443 |
| 2010/0324424 A1 | 12/2010 | Sato | |

OTHER PUBLICATIONS

European Search Report; european Application No. 11 16 2845 filed Apr. 16, 2011; EP Search Completion date Sep. 13, 2011.
L. Morino, "Helmholtz decomposition revisited: Vorticity generation and trailing edge condition", Computational Mechanics (1986) 1, pp. 65-90.
K.E Oughstun, "Helmholtz Theorem" University of Vermont, Retrieved from internet: URL: http://www.cems.uvm.edu/{oughstun/LectureNotes141/Topic_03_%28Helmholtz$27%20Theorem%29.pdf; Retrieved on Sep. 12, 2011, pp. 9 and 12.
S.J Norton, Unique tomographic reconstruction of vector fields using boundary data: IEEE Transactions on Image Processing, vol. 1, No. 3, Jul. 1, 1992, pp. 406-412, XP55006897.
Stephen J. Norton, "Tomographic Reconstruction of 2-D Vector Fields: Application to Flow Imaging" Geophysical Journal International, vol. 97, No. 1, Apr. 1, 1989, pp. 161-168, XP55006898.
Tokuhisa Uejima, "A New Echocardiographic Method for Identifying Vortex Flow in the Left Ventricle: Numerical Validation", Ultrasound in Med. & Biology, vol. 36, No. 5, pp. 772-788, 2010, XP55006547.

* cited by examiner

*Primary Examiner* — Peter Luong
(74) *Attorney, Agent, or Firm* — Cantor Colburn LLP

(57) ABSTRACT

A method and device for transforming a Doppler velocity dataset into a velocity vector field, the including: (a) providing a 2D or 3D Doppler velocity dataset, acquired by means of 2D or 3D ultrasonography from an object; b) calculating a velocity vector field by assuming the velocity at each point of the dataset to be the sum of the provided Doppler velocity and an additional vector field derived from an irrotational flow velocity, and by assuming the velocity vector field to be mathematically continuous, therefore solving an elliptical equation of the Poisson type.

16 Claims, 4 Drawing Sheets

METHOD OF TRANSFORMING A DOPPLER VELOCITY DATASET INTO A VELOCITY VECTOR FIELD

TECHNICAL FIELD

The invention relates to a method for transforming a Doppler velocity dataset into a velocity vector field, and a computer program product, digital medium and device for performing said method.

BRIEF DISCUSSION OF RELATED ART

Blood in the heart and in circulation is expected to flow in a physiological appropriate manner. In presence of a modification, due to pathology or stress, blood immediately responds with a modification of its flow pattern. For example vortices are produced downstream of a stenosis, or stagnating intraventricular circulation is found next to a hypokinetic, ischemic, wall. The ability to evaluate the blood flow pattern would produce information to be used as an additional useful support to improve diagnostic and therapeutic processes. This would be particularly useful if such evaluation could be performed non-invasively.

Non-invasive methods to evaluate blood flow based on MRI have been presented in literature (see Markl et al 2011 for a recent review). These methods based on MRI require substantial large equipments and are not of practical use in clinical routine. In addition, flow calculation requires an acquisition at high frame rate that cannot normally be achieved in MRI.

The velocity of blood flow can be obtained with ultrasound, echographic, equipments that include Doppler acquisition and processing. Indeed the time profile of velocity in a small volumetric region of interest, Pulsed Wave Doppler, is well recorded by Doppler ultrasound. The Doppler technique also permits to cover spatially extended regions. This approach, usually referred as Color Doppler, just because the velocity is displayed color-coded on the echographic image, is largely applied in two-dimensional echography (as described in the textbook by Otto 2000), and since more recently also in 3D echocardiography. Doppler echography is widely used in clinical practice and represents a valuable diagnostic tool. However, Doppler echography has a fundamental limitation: it can measure the velocity along the direction of a scanline, it detects the value of velocity at which blood is moving towards or away from the transducer, but Doppler measurements are blind to motion in the direction transversal to a scanline. In fact while blood can move in any of the three-dimensional directions, and in fact velocity is a three-dimensional vector, an equipment based on the Doppler effect can record only the motion along one single prescribed direction. Novel methods, still based on the Doppler effect, are being introduced to evaluate the velocity vector, however these methods require multiple transducers and are not a practical use.

An alternative approach, based on experimental techniques developed in fluid dynamics research, the so called Particle Image Velocimetry (P.I.V.) allow to evaluate the two-dimensional velocity vector field from B-mode two-dimensional imaging. The application of PIV to echographic images was originally introduced by Kim et al (2004) and later disclosed in (Sengutpa et al 2009). These methods suffer of an intrinsic limitation on the velocity range, and especially they present an important underestimation of large velocities, therefore they are adequate to evaluate streamlines, but they do not allow to properly quantify velocities and the quantities that can be derived from it (Kheradvar et al 2010).

The present invention relates to a method to manipulate the Doppler velocity information, capable to reconstruct the 2D velocity vector field, or the 3D velocity vector field in 3D imaging, from the single distribution of the Doppler velocity component. A prior art method, based on mass conservation, was previously disclosed (Pedrizzetti et al 2007). That technique rigorously reconstructs the part of the flow field that contributes to the flow-rate across orifices; to this purpose the velocity reconstruction is limited to the spatially symmetric profiles and the presence of a symmetry axis plays a fundamental role in the calculation.

A method for the general purpose of velocity vector reconstruction from Doppler was introduced previously, based on the conservation of mass on the image plane (Ohtsuki and Tanaka, 1991); the same method is further described and applied in subsequent publication (Ohtsuki and Tanaka 1996; Uejima et al 2010). Essentially the same method, with minor differences is used in Garcia et al (2010). A different method, based on the same concept but realized with a different technical solution, was also disclosed later (Ohtsulci and Tanaka 1999a, 1999b, 2001).

The method disclosed here follows the same general fluid dynamics background; however it proposes a new technical solution that substantially improves both the physical consistency and the numerical quality of the reconstructed flow. The original formulation permits to naturally combine the novel method with existing information to improve the solution. Its physical consistency permits further exploitation through the derivation of additional fluid dynamics properties and improves diagnostic and therapeutic capabilities based on blood flow.

MATHEMATICAL BACKGROUND

Consider a 2D image scan-plane where the echographic apparatus reports the Doppler velocity at each point X of the plane $V_D(X)$. The velocity is given at each frame time of the acquisition, and at least one image is necessary. The point coordinates X can be expressed in general as the two Cartesian coordinates $X=(x,y)$ or the polar coordinates $X=(r,\theta)$, where the radius r is the distance from the focus and $\theta$ is the sector angle, transversal to the radial direction. FIG. 1 shows the acquired Doppler velocity along a scan line.

The invention is directed toward the evaluation of the 2D velocity vector field V(X) in term of Cartesian components $V_x(X)$, $V_y(X)$, or polar components $V_r(X)$, $V_\theta(X)$.

A few solutions to this problem were previously disclosed (Ohtsuki and Tanaka, 1991; Ohtsuki and Tanaka 1996; Uejima et al 2010; Garcia et al 2010; Ohtsuki and Tanaka, 1999a, 1999b, 2001). The methods employed in these publications are all based on the same general concept and are here summarized. Differences are remarked along with the descriptions.

They consider polar coordinates such that the radial velocity is simply $V_r=-V_D$, and the transversal velocity $V_\theta$ has to be computed. To this aim, the tentative assumption of flow incompressibility on the plane is made, and the transversal coordinate is computed by using the planar continuity equation that in polar coordinates reads $$\frac{\partial r V_r}{\partial r} + \frac{\partial V \partial}{\partial \partial} = 0 \tag{1}$$

Given that the radial velocity is known by the Doppler measurement in the echographic sector ranging from $\theta_1$ to $\theta_2$, the first term in the continuity equation (1) can be computed and the radial velocity is then evaluated using (1) by integration $$V_\vartheta(r, \vartheta) = -\int_{\vartheta_0}^{\vartheta} \frac{\partial r V_r}{\partial r} d\vartheta \qquad (2)$$

where the integration can start from any position, here indicated by $\theta_0$, where the value of the transversal velocity is known.

The approach described above is often expressed making use of the streamfunction $\psi(r, \theta)$ that permits to define the velocities as $$V_r(r, \vartheta) = \frac{1}{r}\frac{\partial \psi}{\partial \vartheta} \quad V_\vartheta(r, \vartheta) = -\frac{\partial \psi}{\partial r} \qquad (3)$$

and it is immediate to show that velocities defined in this way automatically satisfy the continuity equation (1). Using this approach the streamfunction can be evaluated from integration of the known radial velocity and then the transversal velocity from differentiation (3). This leads to exactly the same result (2). In synthesis, all these approaches suggest the use of the continuity equation (2) to compute the transversal velocity component from the radial, or Doppler, velocity. FIG. 2 shows this procedure of reconstruction of the transversal velocity.

Unfortunately, the integration (2) gives the solution apart from an undetermined function of the radial coordinate and of time. In other words, for example, the value of the transversal velocity on one end of the scan sector, at $\theta=\theta_1$ can be imposed, while the value at the other end, at $\theta=\theta_2$, follows from integration (2). Typically, either values needs to be imposed; for example to zero if the sector is wide enough, or to a predefined value of the bounding tissue. In fact, the direct use of (2) gives unrealistic values because incompressibility is not exact, due to the presence of a third cross-plane component, and the use of a first order integration (2) eventually provokes the accumulation of all the errors.

The methods mentioned above propose different solutions to this problem. The most popular solution, initially disclosed in (Ohtsuki and Tanaka, 1991) later reported and refined in (Ohtsuki and Tanaka 1996; Uejima et al 2010) suggests the separation of the Doppler velocity into two components and apply incompressibility on the so-called "vortex" component only, assuming that the other is responsible for cross-plane motion. Other solutions (Ohtsuki and Tanaka, 1999a, 1999b, 2001) introduce a series of sink-source points. The recent proposal (Garcia et al 2010) suggests the integration of (2) along the two directions, and takes the average of the two. In general, mathematically rigorously, the transversal velocity obtained by integration (2) method must be corrected with an arbitrary function that permits to satisfy the boundary conditions at the two ends of the sector. The easiest is that of using a linear correction, which is equivalent to subtracting a function of the radial distance and time, from the Doppler velocity.

Thus, these existing methods present two principal drawbacks:

The conceptual drawback that the continuity equation cannot be satisfied, therefore the solution $V_\theta(r, \theta)$ is—in fact—defined up to an arbitrary function $f(r,\theta)$ that may completely alter the solution. The existing methods essentially suggest a, still arbitrary, choice to define the shape of such a function.

The methodological drawback that the solution is found by integration along each sector separately: the solution at one radial position is computed independently from the solution at another radial position. This is a consequence of using a formulation employing first order partial differential equation. The solutions typically present discontinuities along the radial position.

BRIEF SUMMARY

The invention provides a method which allows a stable, reproducible and accurate calculation of the velocity vector field from Doppler velocity data.

More specifically, the invention provides steps of (a) providing a 2D or 3D Doppler velocity dataset, acquired by means of 2D or 3D echography from an object; (b) calculating a velocity vector field by assuming the velocity at each point of the dataset to be the sum of the provided Doppler velocity and a velocity field based on an irrotational solution, and by assuming the velocity vector field to be mathematically continuous, therefore solving an elliptical equation of the Poisson type.

The Doppler velocity dataset can be 2-dimensional (2D) or 3-dimensional (3D) and the method may be applied on a single such dataset or a sequence of such Doppler velocity datasets acquired from the same object sequentially, e.g. to capture its movement. The Doppler velocity dataset has preferably been acquired previously with suitable ultrasonic/echographic equipment. The aim of the invention is to transform such Doppler velocity field into a physically consistent and mathematically continuous velocity vector field.

Step (a) of providing a Doppler velocity dataset may comprise importing the dataset, reading it from a file, receiving from some network, or streaming, etc.

The object of which the Doppler velocity dataset is acquired is preferably a human or animal body, or part thereof, such as a particular organ or tissue. Most preferably, the velocity dataset is acquired of organs with blood flow, wherein the Doppler velocity dataset mostly shows the flow of blood. Most preferred, the object is the heart or a part thereof, such as the right or left ventricle, the atrium, or alternatively the aortic arc or another major blood vessel.

Usually, the Doppler velocity dataset will show a field of view containing spaces filled with flowing blood, surrounded by other tissue such as the vessel or heart wall. Naturally, the vessel wall will be stationary or move in a different fashion than the blood within.

Once the mathematically continuous velocity vector field has been calculated, it is preferably exported to a means for visualization such as a display or printer, or is used for further processing, storage or other use.

In the following, the mathematical formulae underlying the invention will be explained in more detail.

Consider a 2D scan-plane, or a 3D scan-volume, where the echographic apparatus reports the Doppler velocity at each point X of the plane or volume $V_D(X)$. The velocity is given at each frame time of the acquisition, and at least one image is necessary. FIG. 1 shows the acquired Doppler velocity along a scan line.

It is assumed that the velocity field is given by the Doppler component $V_D(X)$ plus an additional velocity vector field $U'(X)$, derived from an irrotational flow $U(X)$: $V(X)=V_D(X)+U'(X)$. Where the Doppler part is formally expressed as a vector build by the only Doppler (radial in polar coordinates)

component, an expression that is general for arbitrary coordinates. The irrotational flow, U(X), can be expressed as the gradient of a scalar potential $\phi$ as $$U(X) = \nabla \phi \quad (4)$$

The choice of an irrotational flow, sometime called potential flow, is due to the following reasons. A potential flow is the least disturbing flow, in the sense that it does not modify the distribution of vorticity, that is the key quantity in any fluid flow (see for example chapter 12 and 13 in the general fluid dynamics textbook, Panton 2005), therefore is does not significantly alter energy dissipation and shear stresses distribution in the flow field. A potential flow does not enter, beside rigid transport terms, in the fluid dynamics energy balance. Nevertheless, the irrotational flow permits to adjust any lack of continuity, it rather can act on continuity only.

In one embodiment, U'(X)=U(X), i.e. the additional velocity vector field U'(X) is itself irrotational. In other, more general embodiments, the additional velocity vector field takes care of other corrections, but is still derived from or based on an irrotational solution. For example, U'(X) may be a modification of an irrotational flow field to allow compressibility effects or, in the case of 2D Doppler Velocity datasets, out-of-plane motion. For example, the additional vector field U' is obtained from U by increasing or reducing one or more of its individual vector components by a multiplicative factor in order to mimic compressibility effects or out-of-plane motion following experimental observations or theoretical concepts. The multiplicative factor can also be zero for the purpose of eliminating one or more of its vector components.

In another embodiment, U'(X) is build from U(X) by eliminating the radial component (the component parallel to the scanline), such that the radial velocity component is always identical to the original Doppler velocity.

The following mathematical derivation assumes that U(X)=$\nabla \phi$. However, similar solutions apply for a generalised U'(V) which is a modification of an irrotational flow field.

The potential flow permits to satisfy the continuity simply by applying the continuity equation, also called incompressibility constraint, that in general is expressed as $$\nabla \cdot V = 0 \quad (5)$$

that is equivalent to (1) in 2D polar coordinates. The Doppler flow alone does not satisfy the continuity and produces a spatial distribution of divergence. Application of the continuity equation (5) to the complete, Doppler plus potential, flow gives the elliptic equation of Poisson type $$\nabla^2 \phi = -\nabla \cdot V_D \quad (6)$$

where the right-hand side is a known term, computed from the Doppler velocity, and the potential $\phi$ is the unknown. Once the potential is obtained from solution of (6), the total velocity can be computed by (4)—in some embodiments with the additional corrections comprised in U'.

The elliptic equation (6) permits to insert any boundary condition that is physically consistent. It gives exactly the irrotational flow that is physically required to fulfill the continuity constraint and the desired boundary conditions. Methods for the numerical solution of the Poisson-type equation (6) are innumerable. The application of spatial Fourier decomposition, for example, allows developing fast Poisson solvers.

The solution can be performed in the original radial-sector coordinates, the so-called acoustic coordinates that reflect the geometry of the echographic transducer, that are normally similar to the spherical coordinates. This is an optimal choice by an echographic information perspective.

The solution can also be performed in a new set of Cartesian coordinates, the so-called image coordinates that reflect the 2D or 3D effective geometric proportions. This allows to develop calculation techniques that are particularly efficient, and also ensure a more uniform distribution of errors or inaccuracies. This is an optimal choice in terms of numerical processing.

This approach applies equally in 2D and in 3D imaging.

Moreover, in 2D imaging, the continuity equation is not necessarily exactly satisfied because of the presence of cross-plane motion. In this case it is still possible to use the same approach (6) in 2D, but then apply the correction (4) to the transversal component only without correcting the radial velocity from the Doppler measurement. This solution is equivalent to assuming the presence of a cross-plane inflow/outflow that exactly replaces the neglected radial contribution.

This approach solves the two drawbacks previously mentioned:

Conceptually, the correction is simply the solution that is irrotational, does not create new vorticity and thus least modifying the flow, that exactly satisfied the continuity equation, that exactly satisfies the required boundary conditions.

Methodologically, the solution is the result of an elliptic equation, this means that all points of space are connected, and that the solution presents a mathematical regularity. The solution is continuously differentiable along all directions at all points in space. No discontinuity will be produced.

FIG. 3 shows the reconstructed velocity and the regularity difference from the previously disclosed techniques.

BRIEF DESCRIPTION OF THE DRAWINGS

Corresponding elements are designated with corresponding reference signs in the figures.

DETAILED DESCRIPTION

Figure 1:
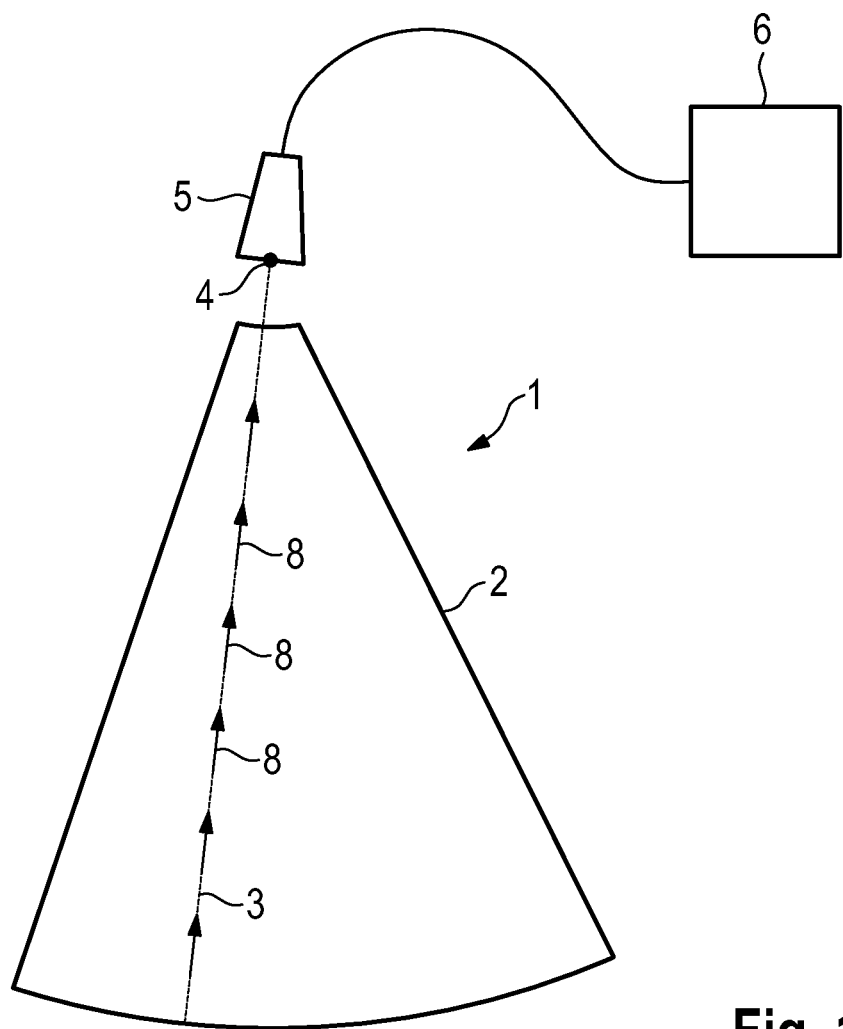
FIG. 1 Schematic plan view of a 2D Doppler velocity dataset.

FIG. 1 is a schematic plan view of a 2D Doppler velocity dataset 1, acquired by means of an ultrasound probe 5 connected to an ultrasound device 6. The conical sector 2 represents the acquisition space or field-of-view, and the Doppler velocity is acquired along all scan-lines 3, which are lines emanating from point 4 on probe 5. One scan-line 3 is shown and a few exemplary Doppler velocity 8 are drawn on top in the shape of arrows.

As stated above, Doppler ultrasound is capable only of measuring the velocity component in the direction of the scan-line. The transverse velocity has to be estimated, which may be done by means of the inventive method.

Figure 2:
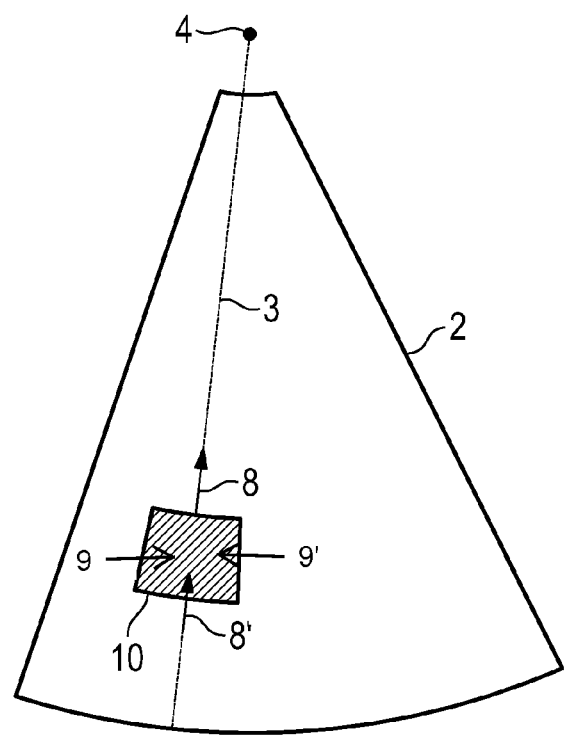
FIG. 2 The same view as FIG. 1, illustrating the concept of mass balance in a sub-region.

FIG. 2 shows the underlying concept of this calculation. The figure shows the same field-of-view 2 and a scan-line 3, as well as two Doppler velocities 8 and 8'. Further shown is a small region 10 at the boundaries of which the Doppler velocities 8 and 8' have been measured. The mass balance in region 10 imposes that when the Doppler velocity increases moving towards the transducer 4, the mass deficit must be supported by the inflow of transversal velocity, here depicted as arrows 9, 9'. Only the increase/decrease of such transversal velocity 9, 9' can be evaluated, the mean transversal velocity remains undefined, or rather has to be defined by imposed boundary conditions. For example, knowledge of the position of a ventrical wall may impose the boundary condition that the velocity perpendicular to said wall is zero.

Figure 3:
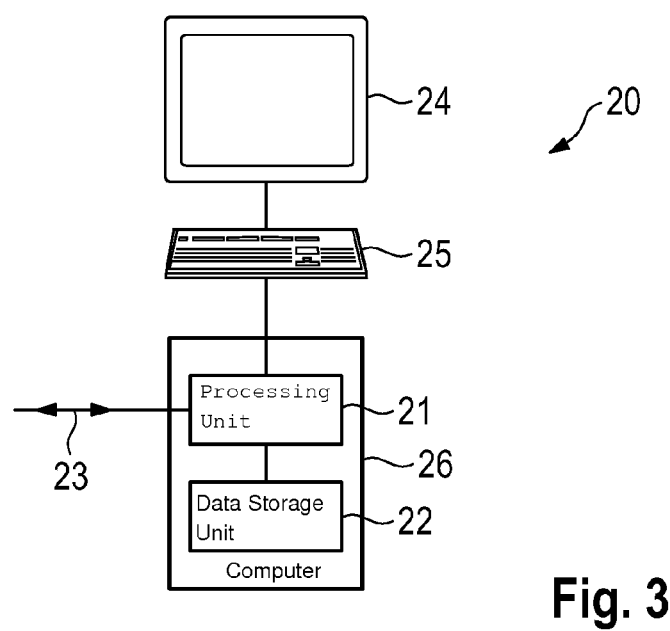
FIG. 3 A schematic view of an embodiment of a device according to the invention.

FIG. 3 depicts schematically a device 20, by which the invention can be carried out. It includes a computer 26, such as a PC or work station, which comprises at least a processing unit 21, such as a CPU, and a data storage 22, such as a hard disk and/or a RAM/working memory. The computer 26 may be connected to a network 23, allowing the importing of the Doppler velocity dataset and exporting of the calculated velocity vector field. Evidently, further standard components such as CD-ROM-drive, DVD-drive, etc. may be present. In addition, the computer may comprise a display 24 for viewing the results, and an input device 25, such as a key-board and/or a mouse.

Figure 4:
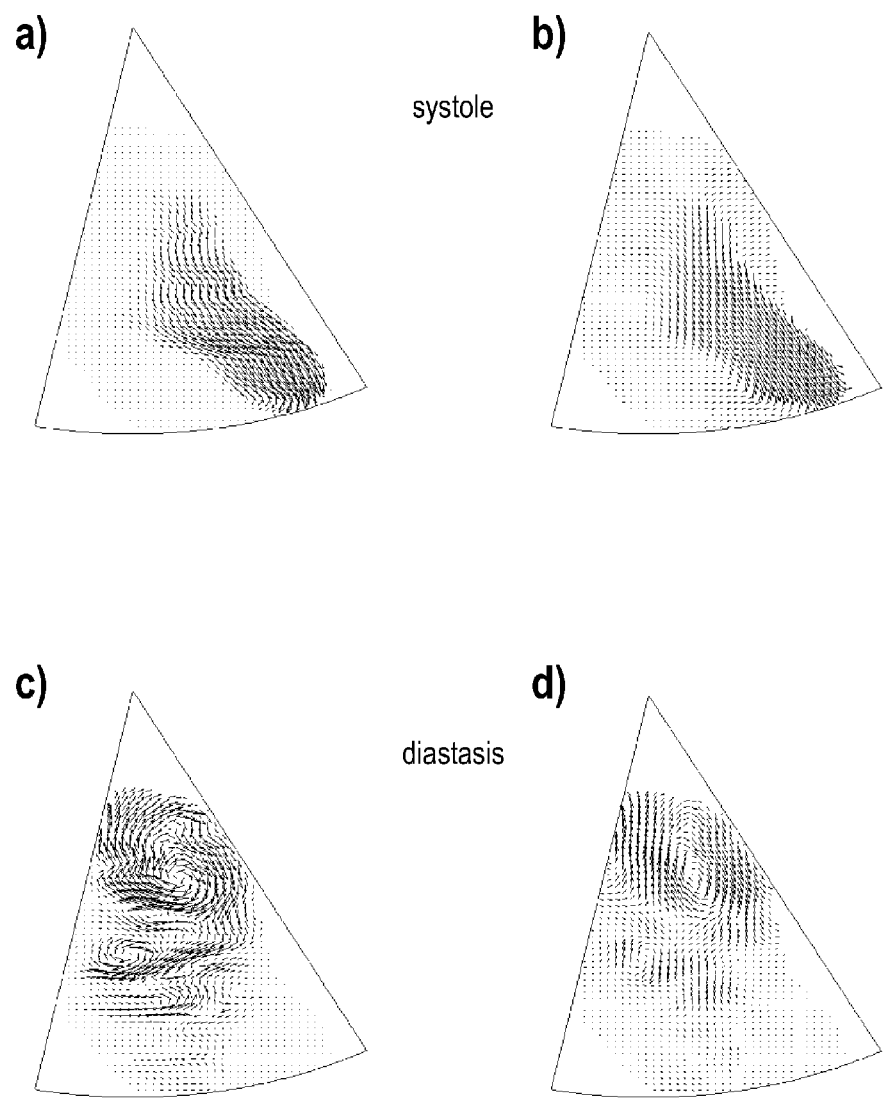
FIG. 4 Representations of 2D velocity fields, calculated from a 2D Doppler velocity dataset as schematically shown in FIG. 1, wherein pictures a and c show the 2D velocity evaluated according to prior art methods, while pictures b and d depict the results of the solution of an elliptical equation according to the invention. The top row (a and b) shows left ventricular blood velocities during systolic contraction, the bottom row (c and d) is during diastasis.

The left side of FIG. 4 shows pictures of 2D velocity fields calculated from a left ventricle of a human heart during systole and diastasis. As is evident from the pictures, the evaluation of the 2D velocity made along transversal direction, for each radial position independently, gives rise to discontinuities, evidenced by horizontal streaks in the left pictures. The same dataset calculated by the method according to the invention, i.e. by solving an elliptical equation of the Poisson type, is shown in the right pictures, demonstrating the regularity of the solution.

Figure 5:
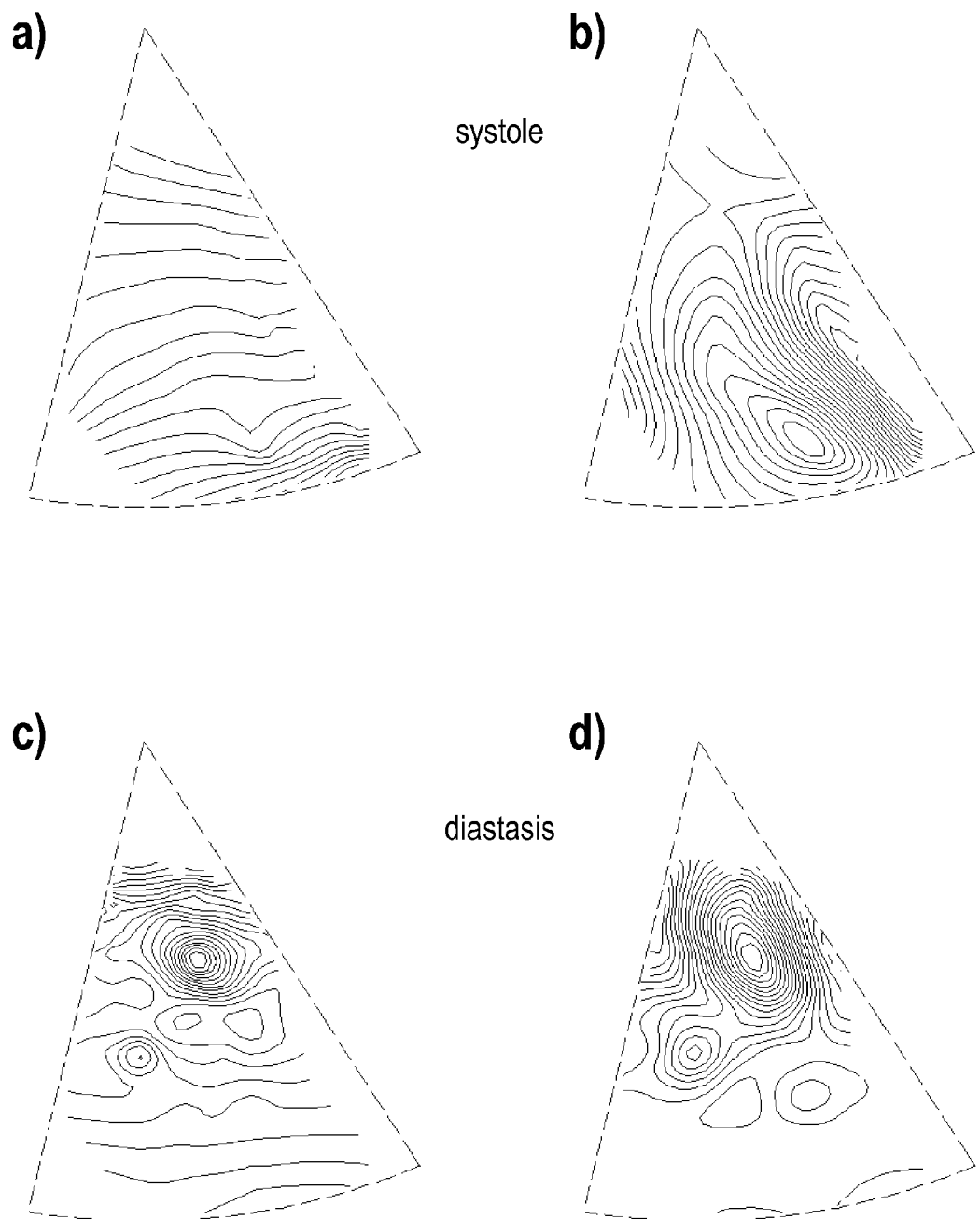
FIG. 5 Shows the spacial distribution of pressure (left column) and vorticity stream function (right column), derived from the velocity vector fields shown in FIG. 4b (during systole) and d (during diastasis).

FIG. 5 demonstrates that further quantities may be derived from the reconstructed velocity vector field, such as the spacial distribution of pressure, shown in the left column, or the vorticity stream function in the right column. Both fields, at both instances, present the regularity properties ensured by the regularity of the elliptically reconstructed vector flow.

In an advanced embodiment, the echographic equipment may simultaneously produce the 2D gray scale B-mode image, with the backscatter from the tissues, and the 2D Doppler velocity data. Or, in 3D imaging, the 3D volumetric grayscale image, and the 3D Doppler velocity data. The gray scale images may be processed by one of the many segmental or tracking techniques that permit the extraction of the tissue motion, or, in the case of static images, simply the extraction of the tissue morphology such as the walls of blood vessels or heart chambers, in order to use this information as boundary condition or internal constraint. For example, a boundary condition may be that the velocity component perpendicular to the wall of the blood vessel is zero. For dynamic images, i.e. where a sequence of 2D or 3D gray scale ultrasound images/datasets are available, these may be processed to extract information on the tissue motion during the sequence, in particular information about the motion of a blood vessel wall.

When this is the case, the congruence between tissue and fluid dynamics can be immediately guaranteed by the formulation previously described. In this case the velocity at portions of the images pertaining to tissues are previously known by the tissue processing, these velocity information are cleared from the Doppler data, if tissue Doppler data are present, and the tissue correction velocities are rewritten in term of gradient of the potential and imposed as immersed boundary conditions in (6) or in place of the elliptic operator.

Such an embodiment ensures a complete congruence between tissue and blood dynamics. It results in a technique that allows to simultaneously analyze the tissue dynamics, the blood pool dynamics, and the coupled fluid-tissue interactive dynamics.

Generally, the inventive method may be carried out on a static Doppler velocity dataset, i.e. where the Doppler velocity has been measured only at one point in time. More preferably, the invention is applied on a sequence of Doppler velocity datasets acquired one after the other, for example during one heart beat.

The irrotational solution is time independent. However, in embodiments using a time sequence of Doppler velocity datasets, time continuity is ensured by the time-continuity of the Doppler measurement, and of the boundary conditions. In other words, the elliptic equation depends on the forcing terms on the equation that are derived from the Doppler velocity and boundary conditions. If these are time-continuous (and they are because they reflect effective time-continuous processes), also the elliptic solution is time-continuous.

Any of the previous embodiments share the property of the evaluation of a blood flow that is consistent with continuity, possibly coupled with the available tissue motion, when available. The technique described above, based on the solution of an elliptic equation, also produces a velocity vector field that has no discontinuities, and that is regular enough to allow the accurate and reliable evaluation of further fluid dynamics quantities that may well correlate with cardiovascular pathophysiology.

In fact, many additional fluid dynamics quantities can be derived from the velocity vector field. However, their evaluation typically requires differential operation of velocity components. Such differential operations, sometime called also spatial derivatives or gradients, necessarily require that the velocity vector field presents sufficient regularity properties; as a minimum requirement is the absence of discontinuities (absence of jumps, step-like behaviour) and derivability (absence of cusps, corners). These regularity properties are intrinsically contained and ensured by the novel method disclosed here.

Examples of such derived quantities include the evaluation of relative pressure fields that, to be correct, should be computed from the Euler equation as the Bernoulli theorem can be used only if integration is made along a streamline, otherwise it implicitly assumes the absence of vorticity in the flow, that is a strong assumption. More rigorously, in the case of a velocity vector field that satisfies mass conservation, the pressure p is evaluated by $$\nabla^2 p = -\nabla \cdot (V \cdot \nabla V) \qquad (7)$$

where the right hand side include a nonlinear combination of derivatives of the velocity vector field. For example, in a 2D field, in Cartesian coordinates, the formula (7) becomes $$\nabla^2 p = 2 \frac{\partial V_x}{\partial x} \frac{\partial V_y}{\partial y} - 2 \cdot \frac{\partial V_y}{\partial x} \frac{\partial V_x}{\partial y} \qquad (8)$$

The ability of an accurate evaluation of relative pressure is especially relevant in cardiovascular diagnosis, because it allows to compute the pressure drops across natural or diseased valves, across stenosis, for example. The knowledge of pressures permits an evaluation of the forces acting on the walls, and can be used as a predictive tool of long-term deformation and remodeling, for example in aneurisms or in the cardiac cavities.

Other examples include the evaluation of shear stresses that are computed by the derivatives of velocity transversally to the direction of motion. In particular the wall shear stress is considered as a primary indicator of the development of arteriosclerosis. Energy dissipation, computed by another combination of velocity derivatives, gives information on the cardiac energy consumption imputable to flow patterns. In general, the development and presence of vortices permits to build indicators of the cardiovascular flow health. Vortices develop after arterial stenosis, they are present inside aneurisms, they develop downstream cardiovascular valves, and are present in the cardiac chambers. Vortices are computed from vorticity, typically indicated with w(X), that is defined as the curl of velocity. In formulas $$\omega = \nabla \times V \qquad (9)$$

that comprises a linear combinations of velocity derivatives. FIG. 5 shows exemplary reconstructed quantities, pressure and vorticity streamfunction in this case.

In general, more simply, the accurate knowledge of the velocity vector field also permits to compute the total flow, or discharge, moving along a vessel or across an orifice. It permits to compute several quantities, like cardiac output, regurgitations, volumes, peak velocities, accelerations etc., that may be relevant in the diagnostic process.

The invention is also directed to a computer program product comprising software code portions for performing the method according to the invention when said product is run on a computer. Such computer program may also be stored on a digitally readable medium such as a hard disk, working memory, diskette or optically readable medium such as a CD-ROM or DVD.

Finally, the invention is also directed to a device which is adapted for performing the method described above, wherein such device may be an ordinary computer, work station or a console of an ultrasound imaging facility.

The invention claimed is:

1. A method for transforming a Doppler velocity dataset into a velocity vector field, the method comprising the steps of:
   a) performing at least one of a 2D and a 3D ultrasound of an object to obtain at least one of a 2D and a 3D Doppler velocity dataset;
   b) calculating a velocity vector field by assuming a velocity at each point of the at least one of the 2D and the 3D Doppler velocity dataset to be a sum of a provided Doppler velocity from the performing at least one of a 2D and a 3D ultrasound and an additional vector field derived from an irrotational flow velocity obtained by solving an elliptical equation of the Poisson type configured to ensure that the velocity vector field is mathematically continuous; and
   c) generating and displaying an image of the calculated velocity vector field representing the blood flow in a blood vessel or chamber of a heart.

2. The method of claim 1, wherein the sum of the provided Doppler velocity and the additional vector field derived from the irrotational flow velocity is defined as:

$$V(X) = V_D(X) + U(X)$$

where X denotes a point in 2D or 3D space, V(X) is a velocity of the velocity vector field to be calculated, VD(X) is the provided Doppler velocity, and U(X) is the irrotational flow velocity, wherein ensuring that the velocity vector field is mathematically continuous implies that:

$$\nabla \cdot V = 0$$

and the elliptical equation of the Poisson type is $$\nabla^2 \phi = -\nabla \cdot V_D$$

where $\phi$ is a potential field defining the irrotational flow velocity field by $$U(X) = \nabla \phi,$$

and wherein V(X) is calculated in step b) for each pixel/voxel in the at least one of the 2D and the 3D Doppler velocity dataset by solving the above equations.

3. The method of claim 2, wherein calculating the velocity vector field includes assuming that a radial component of U(X) is zero, such that a radial component of V(X) is always equal to the provided Doppler velocity, where the radial component corresponds to a direction of a scan line of the ultrasound.

4. The method of claim 3, wherein at least one of the 2D and the 3D Doppler velocity dataset is a 2D Doppler velocity dataset configured to mimic an out-of-plane motion of the velocity vector field.

5. The method of claim 1, wherein the sum of the provided Doppler velocity and the additional vector field derived from the irrotational flow velocity is defined as $$V(X) = V_D(X) + U'(X)$$

where X denotes a point in 2D or 3D space, V(X) is a velocity of the velocity field, VD(X) is the provided Doppler velocity, and U'(X) is the additional vector field derived from the irrotational flow velocity U(X) that satisfies an incompressibility constraint $$\nabla \cdot (V_D + U) = 0$$

wherein the additional vector field U' is obtained from U after increasing or reducing one or more of its individual vector components by a multiplicative factor in order to mimic compressibility effects following experimental observations or theoretical concepts, and wherein V(X) is calculated in step b) for each pixel/voxel in the at least one of the 2D and the 3D Doppler velocity dataset by solving above equations.

6. The method of claim 5, wherein calculating the velocity vector field includes assuming that the radial component of U'(X) or U(X) is zero, such that a radial component of V(X) is always equal to the provided Doppler velocity, where the radial component corresponds to a direction of a scan line of the ultrasound.

7. The method of claim 1, wherein the object is an organ of a human or animal body with blood flow.

8. The method of claim 1, wherein the at least one of the 2D and the 3D Doppler velocity dataset represents blood flow in a blood vessel or chamber of a heart.

9. The method of claim 1, further comprising:
   c) providing at least one of a 2D and a 3D greyscale ultrasound dataset of the object, the at least one of the 2D and the 3D greyscale ultrasound dataset covering at least approximately a same field-of-view as the at least one of the 2D and the 3D Doppler velocity dataset, d) processing the at least one of the 2D and the 3D greyscale ultrasound dataset to extract information on a tissue morphology on walls of blood vessels or heart chambers, and e) using the tissue morphology information extracted in step d) in step b) as a boundary condition or internal constraint, for calculating the velocity vector field for each pixel/voxel in the at least one of the 2D and the 3D Doppler velocity dataset.

10. The method of claim 1, wherein the object is a moving object, and the method further comprises:
providing a sequence of the at least one of the 2D and the 3D Doppler velocity datasets acquired from the moving object at sequential time points, and
performing step b) at each sequential time point.

11. The method of claim 1, wherein the object is a moving object, and the method further comprises:
   c) providing a sequence of 2D or 3D greyscale ultrasound datasets acquired from the moving object at sequential time points, each dataset covering at least approximately a same field-of-view as the at least one of the 2D and the 3D Doppler velocity dataset,
   d) processing the sequence of 2D or 3D greyscale ultrasound datasets to extract information on tissue motion within the sequence of 2D or 3D grayscale ultrasound datasets, the tissue motion corresponding to a motion of a blood vessel or heart chamber wall, and
   e) using the tissue motion information extracted in step d) in step b) as boundary condition or internal constraint for calculating the velocity vector field for each pixel/voxel in the at least one of the 2D and the 3D Doppler velocity dataset.

12. The method of claim 1, further comprising:
calculating from the velocity vector field at least one of relative pressure, shear stresses, energy dissipation, vorticity, discharge volume, cardiac output, amount of regurgitation in a heart, total flow along a blood vessel or heart chamber or through an orifice, peak velocity, and acceleration.

13. The method of claim 1, wherein the object is a chamber of a heart, and the method further comprises:
calculating from the velocity field vector in step b) at least one force acting on walls of the chamber of the heart, and shear stresses in the wall of the chamber of the heart.

14. The method of claim 1, further comprising generating an image of the calculated velocity vector field.

15. A non-transitory computer readable medium having stored thereon software code portions for performing the method according to claim 1 when said software code portions stored on the non-transitory computer readable medium are executed on a computer.

16. A device, comprising a memory for storing data and instructions, and a processor structured to execute the instructions to perform the method of claim 1.

* * * * *